United States Patent [19]
Maguire et al.

[11] Patent Number: 5,957,961
[45] Date of Patent: Sep. 28, 1999

[54] MULTIPLE SENSOR, TEMPERATURE CONTROLLED R-F ABLATION SYSTEM

[75] Inventors: Mark A. Maguire, San Jose; Kevin C. Ladd, Redwood City; John W. Gaiser, Mt. View; Le T. Le, San Jose, all of Calif.

[73] Assignee: Medtronic, Inc., Minneapolis, Minn.

[21] Appl. No.: 09/005,405

[22] Filed: Jan. 9, 1998

Related U.S. Application Data

[62] Division of application No. 08/613,298, Mar. 11, 1996, Pat. No. 5,755,760.

[51] Int. Cl.$^6$ .................................................. A61N 1/08
[52] U.S. Cl. ............................ 607/99; 607/102; 607/113; 600/549; 606/42
[58] Field of Search ..................................... 607/101, 102, 607/96, 99, 98, 100, 113, 116, 122; 600/549; 606/41, 42, 31, 27

[56] References Cited

U.S. PATENT DOCUMENTS

| | | |
|---|---|---|
| 4,940,062 | 7/1990 | Hampton et al. . |
| 4,960,411 | 10/1990 | Buchbinder . |
| 5,083,565 | 1/1992 | Parins . |
| 5,122,137 | 6/1992 | Lennox . |
| 5,254,088 | 10/1993 | Lundquist et al. . |
| 5,304,131 | 4/1994 | Paskar . |
| 5,318,525 | 6/1994 | West et al. . |
| 5,354,297 | 10/1994 | Avitall . |
| 5,358,479 | 10/1994 | Wilson . |
| 5,383,852 | 1/1995 | Stevens-Wright . |
| 5,487,757 | 1/1996 | Truckai et al. . |
| 5,545,200 | 8/1996 | West et al. . |
| 5,578,007 | 11/1996 | Imran . |
| 5,603,697 | 2/1997 | Grundy et al. . |
| 5,688,267 | 11/1997 | Panescu et al. ........................ 607/102 |
| 5,769,847 | 6/1998 | Panescu et al. ........................ 607/101 |
| 5,810,802 | 9/1998 | Panescu et al. ........................ 607/101 |

FOREIGN PATENT DOCUMENTS

| | | |
|---|---|---|
| 0617916 | 10/1994 | European Pat. Off. . |
| 0605796 | 1/1996 | European Pat. Off. . |
| 9411059 | 5/1994 | WIPO . |
| 9510322 | 4/1995 | WIPO . |

OTHER PUBLICATIONS

Cox et al, "A review of Surgery for Atrial Fibrillation", Journal of Cardiovascular Electrophysiology, vol. 2, No. 6, Dec. 1991 p. 541.

Feld et al., "Radiofrequency Catheter Ablation for the Treatment of Human Type 1 Atrial Flutter", Circulation, vol. 86, No. 4, Oct. 1992 p. 1233.

*Primary Examiner*—Kennedy J. Schaetzle
*Attorney, Agent, or Firm*—Reed A. Duthler; Harold R. Patton

[57] ABSTRACT

A catheter ablation system including a catheter having a distal segment carrying at least one electrode extending along the segment and having a number of temperature sensors arranged along the distal segment adjacent the electrode, each providing an output indicative of temperature. The catheter is coupled to a power source which provides R-F energy to the electrode and with temperature processing circuitry coupled to the temperature sensors and the power source which controls power output from the power source as a function of the outputs of the temperature sensors. In a preferred embodiment, the temperature processing circuitry includes circuitry for comparing the temperature indicated by the temperature sensors to a known reference sensor and circuitry for disabling subsequent use of an output of one of the sensors if the output from the sensor differs from the referenced temperature by more than a defined value. In an alternative preferred embodiment, the temperature processing circuitry includes circuitry responsive to the rate of change of the output of the temperature sensors and circuitry for disabling a sensor if the output of the sensor changes at a rate greater than a defined referenced rate of change.

6 Claims, 14 Drawing Sheets

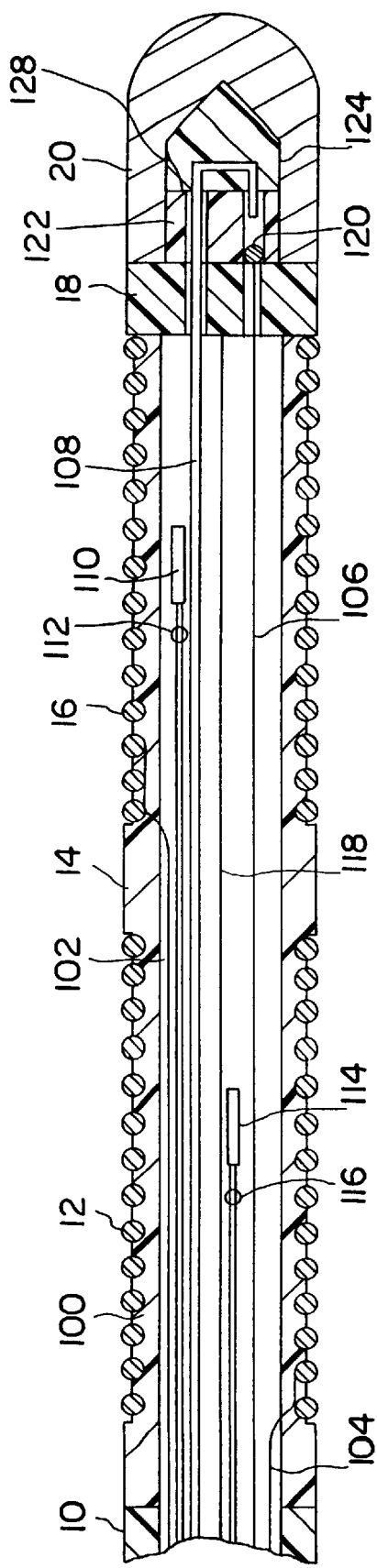
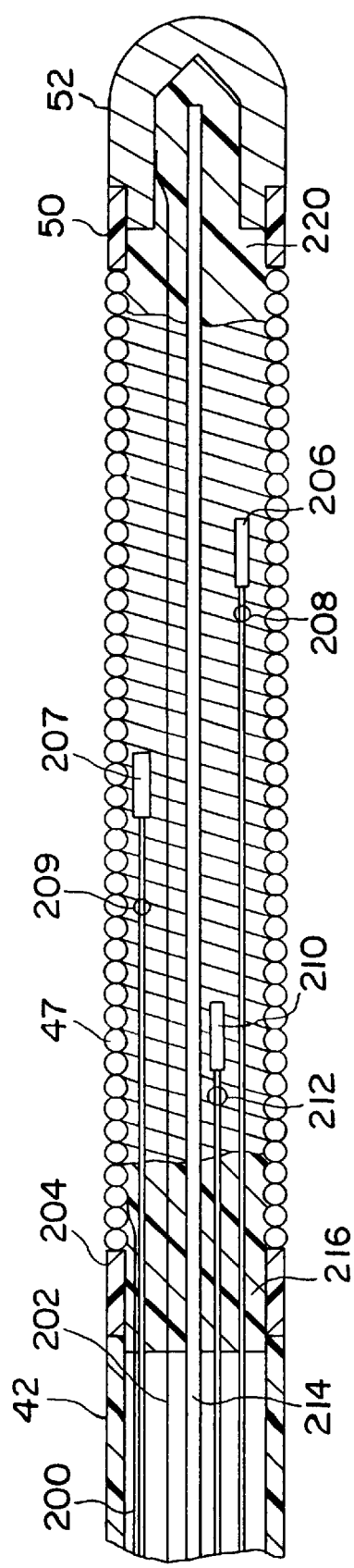
FIG. 3
FIG. 4

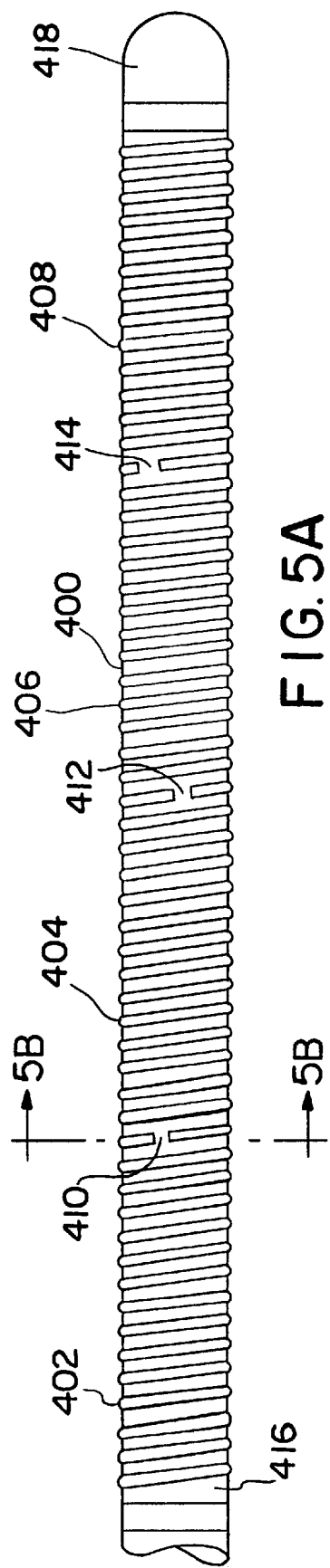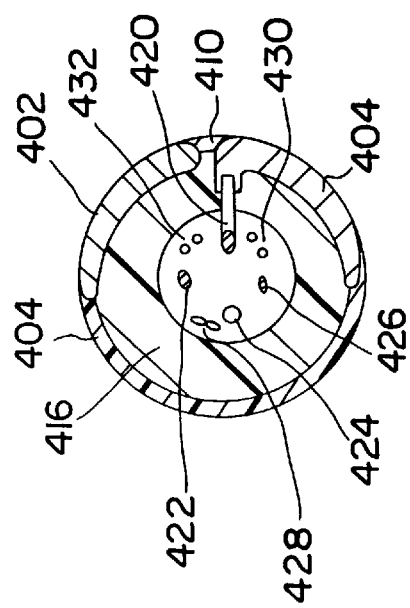
FIG. 5A
FIG. 5B

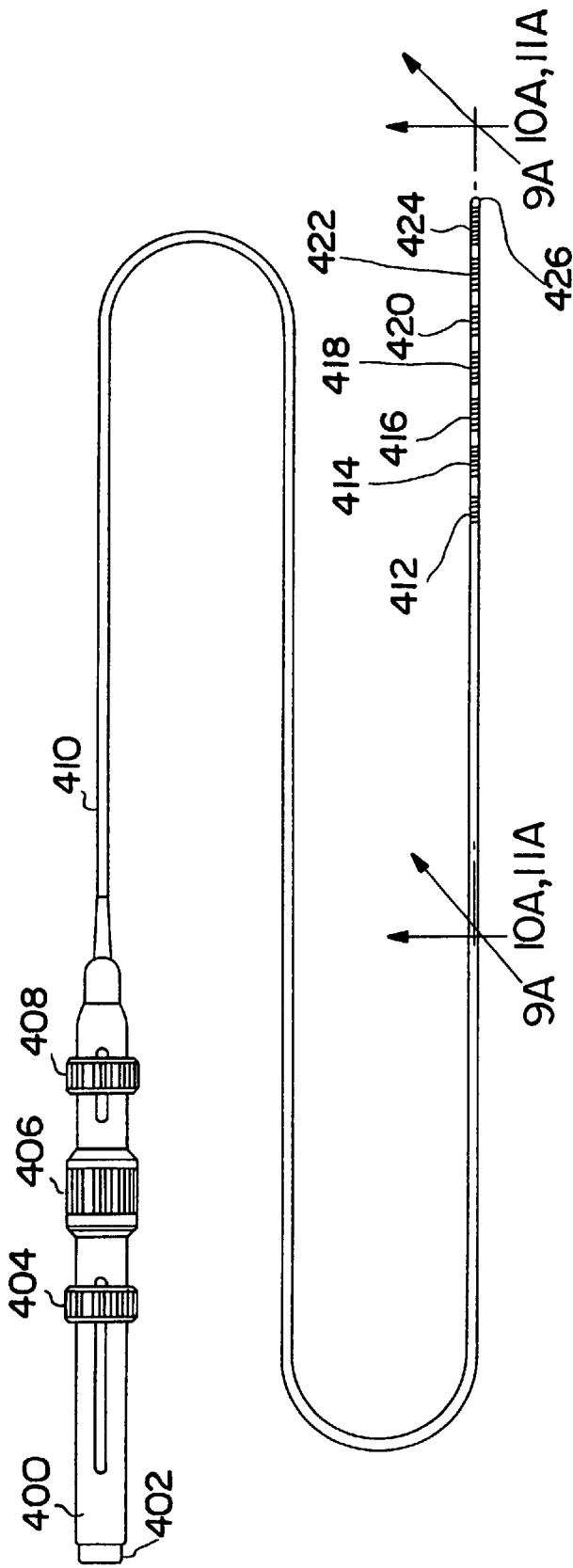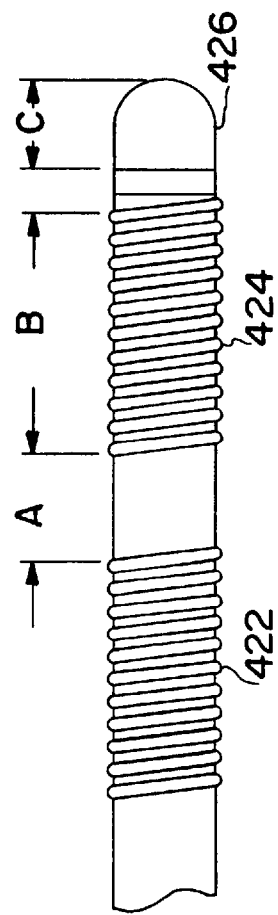
FIG.6A
FIG.6B

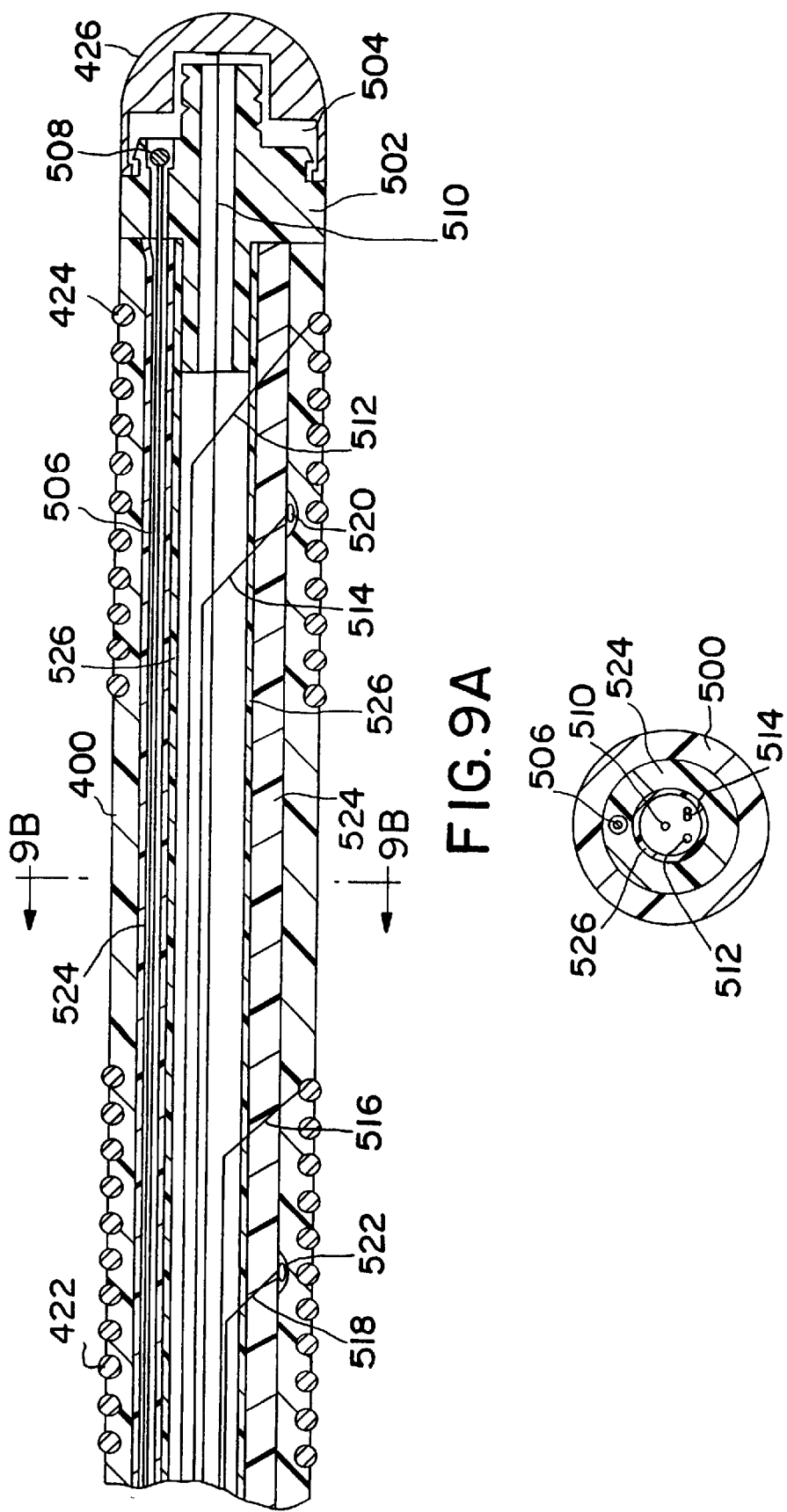

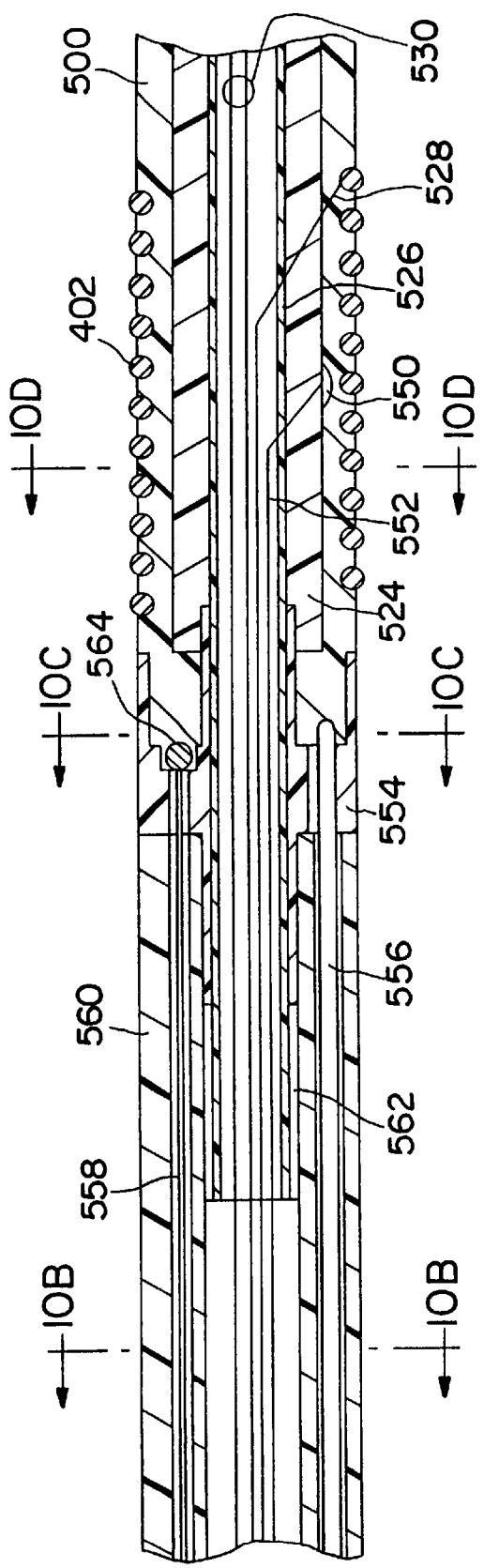
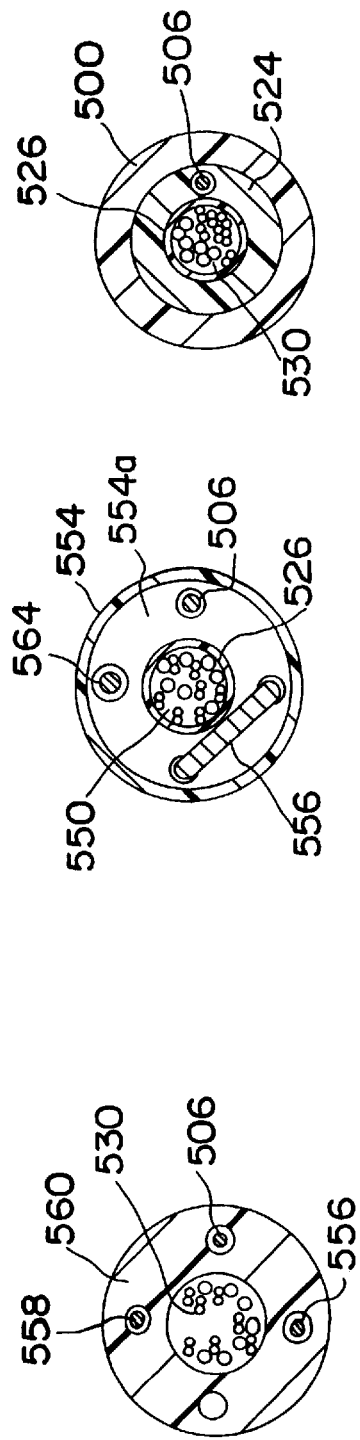
FIG.10A
FIG.10D
FIG.10C
FIG.10B

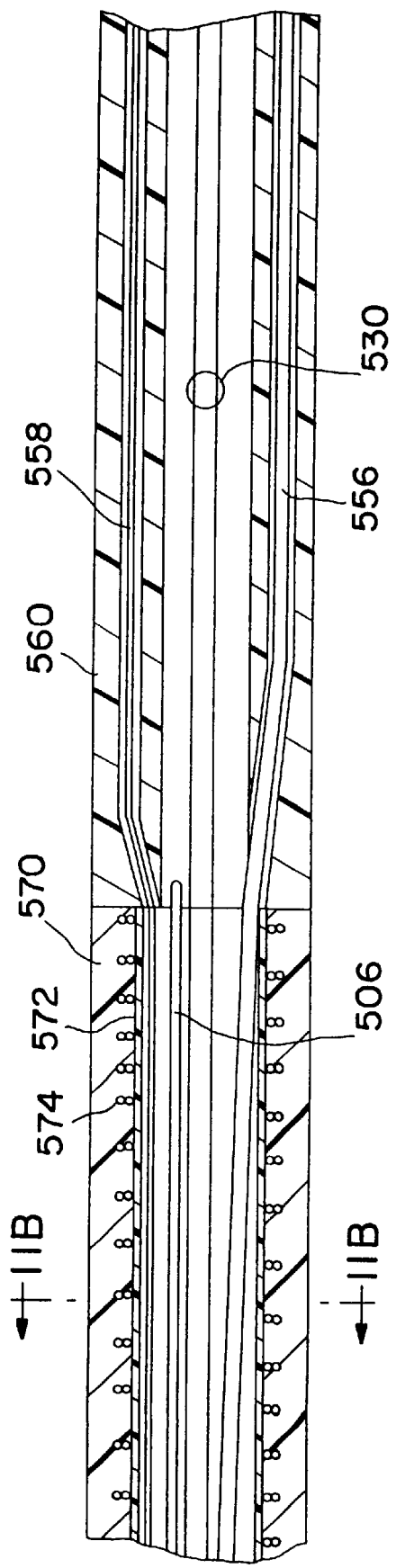
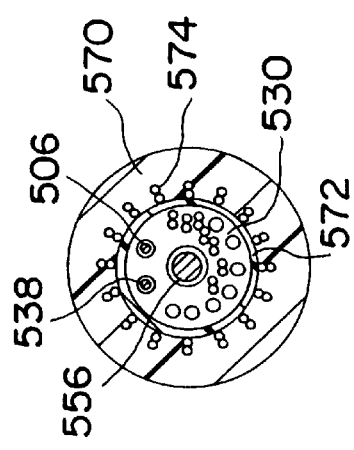
FIG. IIA
FIG. IIB

MULTIPLE SENSOR, TEMPERATURE CONTROLLED R-F ABLATION SYSTEM

This application is a division of application Ser. No. 08/613,298, filed Mar. 11, 1996, now U.S. Pat. No. 5,755,760.

BACKGROUND OF THE INVENTION

This invention relates generally to the field of devices for cardiac surgery, and more specifically to devices for R-F ablation of cardiac tissue.

The present invention is directed toward treatment of tachyarrhythmias, which are heart rhythms in which an chamber or chambers of the heart exhibit an excessively fast rhythm. In particular, the present invention is directed toward treatment of atrial arrhythmias which result from the presence of macro and/or micro-reentrant wavelets (e.g. atrial flutter and atrial fibrillation) and treatment of ventricular tachycardia.

Therapies have been developed for treating tachycardias by destroying cardiac tissue containing identified ectopic foci or aberrant conduction pathways. A variety of approaches have been taken, including application of electrical energy or other forms of energy to destroy the undesired cardiac tissue. As examples, ablation of cardiac tissue has been accomplished by means of radio frequency electrical current, direct current, microwave energy, heat, electrical pulses, cryothermy, and lasers. At present, ablation using R-F energy is perhaps the most widely practiced in the context of ablation procedures that can be carried out by means of a catheter, inserted into the closed heart.

Most R-F ablation catheters employ electrodes which are intended to contact the endocardium of the heart, or, as in U.S. Pat. No. 5,083,565, are intended to penetrate the endocardium and enter the myocardium. In general, R-F ablation catheters are effective to induce small lesions in heart tissue including the endocardium and inner layers of myocardium, in the immediate vicinity of the electrode. However, the medical community has expressed a desire for devices which produce larger and/or longer lesions, to reduce the number of applications of energy (burns) required to effectively ablate cardiac tissue associated with more complex arrhythmias such as atrial flutter or atrial fibrillation and ventricular tachycardia.

R-F ablation causes tissue in contact with the electrode to heat through resistance of the tissue to the induced electrical current therethrough. The actual extent of heating is somewhat unpredictable. However, temperature tends to rise as the duration and amplitude of the R-F signal increase. Heating of the tissue beyond a certain point can cause dissection or charring of the tissue, resulting in a high impedance between the R-F electrode and the return electrode, which in turn leads to cessation of the heating process, and, in some cases, causes the electrode to stick to the charred tissue. One response to this phenomenon has been the inclusion of thermocouple within the ablation electrode, in conjunction with feedback control to modulate the R-F signal to maintain the electrode temperature at a set parameter. One such system is disclosed in U.S. Pat. No. 5,122,137.

Particularly in the context of treating macro and/or micro-reentrant atrial arrhythmias, it has been proposed to create elongated lesions, to define a line of tissue which blocks the passage of depolarization wavefronts. This has, in some cases been accomplished by means of a series of small, individual lesions, each produced by a separate application of R-F energy. As disclosed in U.S. patent application Ser. No. 08/302,304 by Mulier et al, for a "Method and Apparatus for R-F Ablation", it has been proposed that an elongated, coil electrode might instead be employed to produce an elongated lesion with a single application of R-F energy. An elongated coil ablation electrode is also disclosed in published PCT application No. WO94/11059 for a "Fluid Cooled Ablation Catheter, by Nardella.

SUMMARY OF THE INVENTION

The present invention is directed toward expanding and improving the clinical applicability of R-F ablation, by accurately determining the ablation site and by increasing the overall size and extent of the lesions induced by R-F ablation. These goals are pursued by means of an ablation catheter employing one or more electrodes extending of substantial length, located adjacent the distal end of the catheter, in conjunction with a temperature control system employing multiple temperature sensors, arranged along the electrode or electrodes.

In one preferred embodiment, the electrode or electrodes extend over a distal segment of the catheter body, and multiple thermocouples or other temperature sensors are provided along the distal segment. The thermocouples may be used to individually regulate the power applied to individual electrodes along the distal segment. Alternatively, the temperature sensors may be used together to regulate the power applied to the electrode or electrodes, for example by employing the highest measured temperature to control the power applied to one or more electrodes.

In another preferred embodiment, the catheter may be provided with a mechanism for deflecting the distal segment of the catheter body, to provide directional control to the catheter, facilitating placement of its ablation electrode or electrodes at a desired location in the heart, and in close contact with heart tissue. Deflection may be accomplished, for example, by means of internal control wires which induce a curvature in the catheter body when displaced longitudinally. Alternatively, the distal portion of the catheter body may be preformed to display a curved configuration, and may be delivered through a guide catheter. In this case, the distal portion of the catheter body displays its preformed curve as it is advance out the distal end of the guide catheter. In a another preferred embodiment, the catheter body may display a generally straight configuration, with the distal portion located in the heart by means of a deflectable guide catheter, which may provided with internal control wires which allow the distal end of the guide catheter to be deflected.

The features of the embodiments discussed above may also be provided in catheters provided with mapping electrodes, allowing for mapping and ablation to be performed with the same catheter. Similarly, the features of the above described embodiments may also be combined with one another, if desired.

BRIEF DESCRIPTION OF THE DRAWINGS

FIG. 3 is a side, sectional view through the distal portion of the catheter illustrated in FIG. 1.

FIG. 4 is a side, sectional view through the distal portion of the catheter illustrated in FIG. 2.

FIG. 5a is a side view of the distal portion of an additional alternative embodiment of a multiple electrode catheter.

FIG. 5b is a cross sectional view of though the distal portion of the catheter illustrated in FIG. 5a. the catheter illustrated in FIG. 1.

FIG. 6a is a side view of the distal portion of an additional alternative embodiment of a multiple electrode catheter.

FIG. 6b is an enlarged side view of the distal portion of the catheter illustrated in FIG. 6a.

FIGS. 7a–7d illustrates in-plane deflection of the catheter illustrated in FIG. 6a.

FIG. 8 illustrates out-of-plane deflection of the catheter illustrated in FIG. 6a.

FIG. 9a illustrates a side, sectional view through the distal tip of the catheter illustrated in FIG. 6a.

FIG. 9b illustrates a cross sectional view through the portion of the catheter illustrated in FIG. 9a.

FIG. 10a illustrates a side, sectional view through the portion of the catheter proximal to that illustrated in FIG. 9a.

FIGS. 10b–10d illustrate cross sectional views through the portion of the catheter illustrated in FIG. 10a.

FIG. 11a illustrates a side, sectional view through the portion of the catheter proximal to that illustrated in FIG. 10a.

FIG. 11b illustrates a cross sectional view through the portion of the catheter illustrated in FIG. 11a.

FIG. 12b illustrates a distal end view of the catheter of FIG. 12a.

DETAILED DESCRIPTION OF THE PREFERRED EMBODIMENTS

Figure 1:
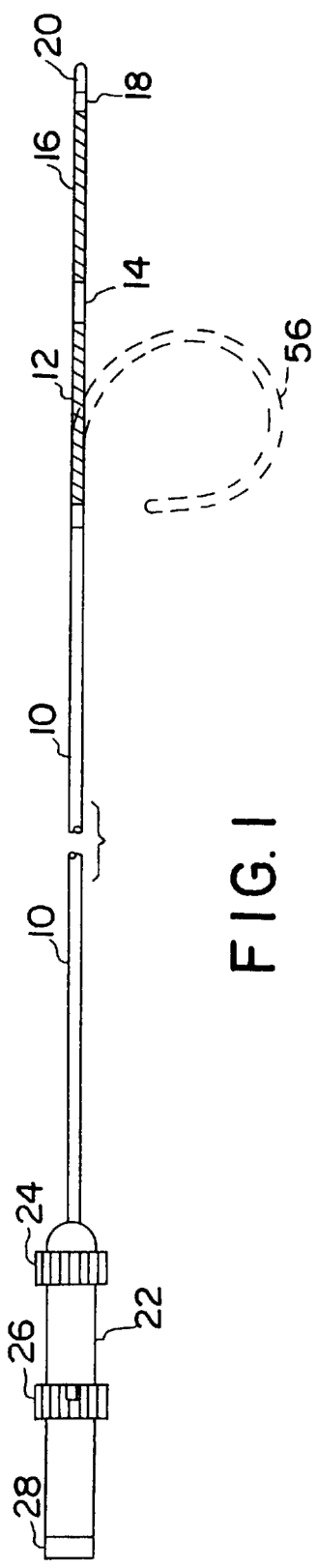
FIG. 1 is a plan view of a first embodiment of a catheter employing the present invention.

FIG. 1 illustrates a plan view of a first catheter adapted to practice the present invention. The catheter is provided with an elongated polymeric catheter body 10, which carries a first elongated coil electrode 12, a second elongated coil electrode 16 and a tip electrode 20 at its distal end. Electrodes 12 and 16 are separated by an insulative segment 14. Electrodes 16 and 20 are separated by a second insulative segment 18. Electrodes 12 and 16 are employed as ablation electrodes, with electrode 20 employed primarily for cardiac mapping. Additional mapping electrodes may optionally be added between electrodes 12 and 16 and/or proximal to electrode 12. Located at the proximal end of the catheter body 10 is a control handle 22, which carries two control knobs 24 and 26. Control knobs 24 and 26 may be employed to deflect the catheter into a curved configuration, as illustrated by broken outline 56, by means of longitudinal displacement of a tension wire. The tension wire, not illustrated, is coupled to knob 24. The catheter tip may also be configured to display a three dimensional configuration, by rotation of an internal core wire (not visible in this view), coupled to knob 26. The proximal end of handle 22 carries an electrical connector 28, including connections for coupling to electrodes 12, 16 and 20 as well as connections for coupling to two or more temperature sensors such as thermocouples or thermistors located internal to the catheter, adjacent electrodes 12 and 16 and optionally electrode 20. The operation of the steering end deflection mechanism of the present catheter corresponds to that disclosed in U.S. Pat. No. 5,318,525 issued on Jun. 7, 1994 and incorporated herein by reference in its entirety. However, other mechanisms for steering or deflecting the distal end of a catheter according to the present invention may also be employed. For example, the steering and deflection mechanism as set forth in U.S. Pat. No. 5,487,757 issued on Jan. 30, 1996 may also be employed to deflect the distal tip of the catheter, as well as any other known deflection/steering mechanism. Similarly, a sliding core wire for adjustment of the radius of curvature of the catheter when deflected may also be employed, as also disclosed in U.S. Pat. No. 5,487,757.

Figure 2:
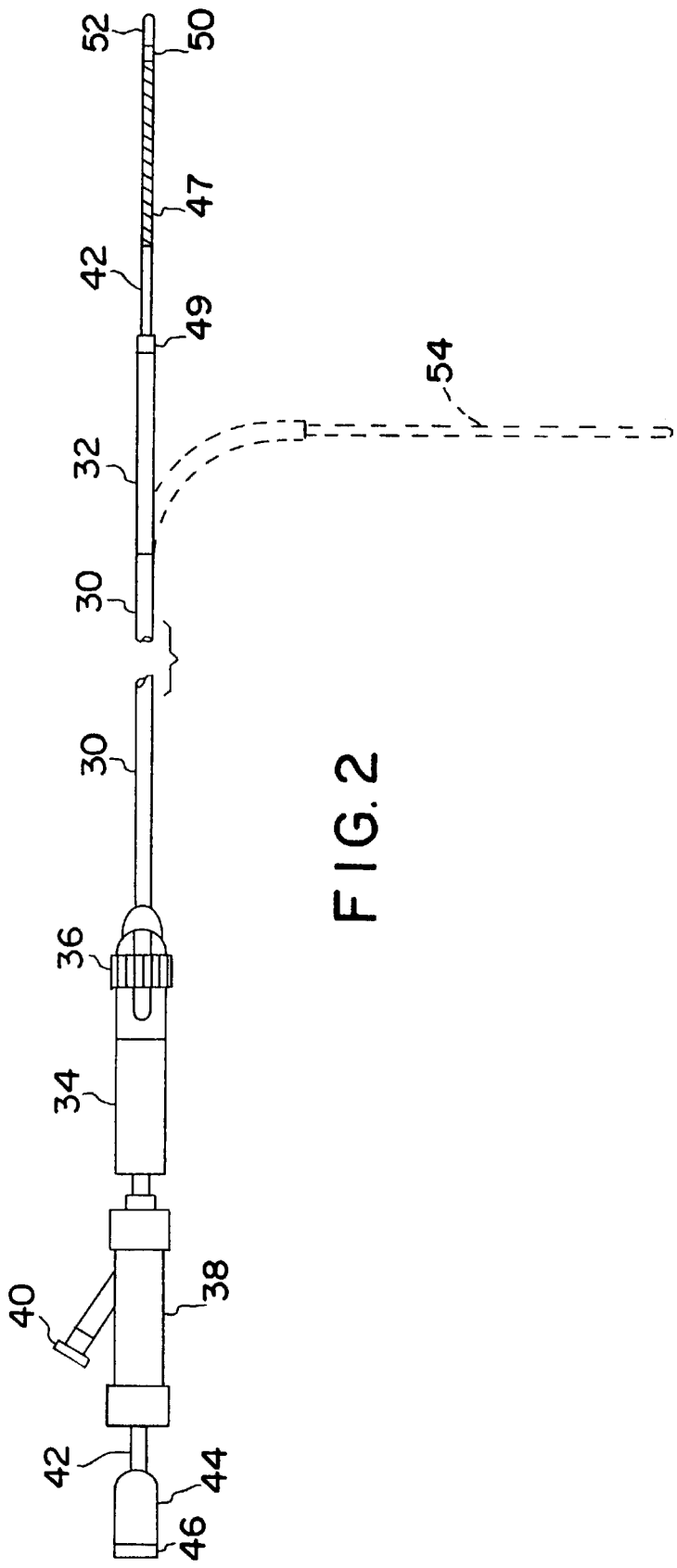
FIG. 2 is a plan view of a second embodiment of a catheter employing the present invention.

FIG. 2 illustrates a side, plan view of a second embodiment of a catheter for use in practicing the present invention. In this embodiment, the catheter takes the form of an ablation catheter, mounted within a deflectable guide catheter. The deflectable guide catheter is provided with an elongated tubular body 32, including a central bore, through which the ablation catheter is passed. The distal portion 32 of the guide catheter may be deflected, as illustrated by broken-out line at 54. Deflection of the distal tip of the guide catheter is accomplished by longitudinal displacement of an internal tension wire, by means of knob 36, located on handle 34 at the proximal end of the guide catheter. In the context of the present invention, any known, deflectable guide catheter may be employed in conjunction with the present invention. For example, U.S. Pat. No. 4,960,411, issued on Oct. 2, 1990, and U.S. Pat. No. 5,304,131, issued on Apr. 19, 1994, both of which are incorporated herein by reference in their entireties, provide examples of deflectable guide catheters of the type which may be employed in conjunction with the present invention. The distal end of the guide catheter optionally carries a ring electrode 49, which may be employed for mapping or ablation. Alternatively, a pair of ring electrodes might instead be provided for mapping and ablation. The proximal end of handle 34 carries a Y fitting 38 which includes a side port 40, for fluid injection into the central lumen of the guide catheter.

The ablation catheter itself is provided with an elongated catheter body 42, which carries an elongated coil electrode 47 and optionally a tip electrode 52. An insulative segment 50 separates coil electrode 47 from tip electrode 52, if present. If tip electrode 52 is deleted, a pliant plastic tip of similar configuration may be substituted. Electrode 47 is employed as an ablation electrode. Electrode 52 if present is employed primarily for cardiac mapping. The proximal end of the ablation catheter exits the proximal end of Y fitting 38, where the proximal portion of the catheter body 42 is visible. An electrical connector 44 is mounted to the proximal end of the catheter body and carries an electrical connector 46, allowing independent connection to electrodes 47 and 52, as well as connection to two or more temperature sensors, located internal to the catheter.

FIG. 3 shows cross-sectional view through the distal end of catheter illustrated in FIG. 1. The drawing is not proportional, but is intended to illustrate the functional interrelation of the components within the catheter. Exemplary dimensions for the catheter may be, for example, a diameter of 5–7 french, coil electrodes 12 and 16 of approximately 5–20 mm in length located on an insulative catheter body tube 100, with a spacing of approximately 1–3 mm between electrodes 12 and 16, a spacing of approximately 2 mm between electrodes 16 and 20, and a length of approximately 1–2 mm for electrode 20. Other numbers of electrodes, electrode sizes and electrode spacings may also usefully be employed. For example four coil electrodes, each 5–10 mm in length may be substituted, with a corresponding additional temperature sensor associated with each additional electrode. Tube 100 is preferably formed of a temperature resistant, flexible, body compatible material such as silicone rubber, with the coils of the electrodes partially embedded therein, similar to currently available transvenous defibrillation electrodes.

Electrode 12 is coupled to the electrical connector at the proximal end of the lead by means of an insulated wire 104. Electrode 16 is coupled to the electrical connector at the proximal end of the catheter by an insulated wire 102. A first thermocouple or thermistor 114 is located within tube 100, adjacent electrode 12. Thermocouple or thermistor 114 is coupled to the electrical connector at the proximal end of the catheter by means of insulated wires 116. A second thermocouple or thermistor 110 is located within tube 100 adjacent electrode 16, and is coupled to the electrical connector at the proximal end of the catheter by means of insulated wires 112.

Located at the distal end of tube 100 is molded plastic insulator 18, which contains bores 120, 122 through which the core wire 108 and tension wire 106 pass. The distal end of core wire 108 is folded back, and anchored within spacer 18, so that rotational force applied to the proximal end of coil wire 108 will be transmitted to the distal tip of the catheter. Ball 121, fixed to the distal end of tension wire 106, allows for tensile force to be applied to the distal end of the catheter. As described in the above-cited U.S. Pat. No. 5,318,525, longitudinal movement of tension wire 106 provides for deflection and straightening of the distal portion of the catheter, coplanar to the catheter body. Rotation of core wire 108, while tension is applied to tension wire 106 provides for lateral deflection of the distal portion of the catheter, so that it is no longer coplanar with the catheter body and defines a three dimensional configuration. Also visible at 128 is the distal end of the third of insulated wire 118, which couples tip electrode 20 to the electrical connector at the proximal end of the catheter.

FIG. 4 illustrates a side, sectional view through the distal tip of the ablation catheter illustrated in FIG. 2. In this figure, electrodes 47 and 52, catheter body 42 and insulator 50 correspond to correspondingly labeled structures in FIG. 2. In this view it can be seen that, like the catheter illustrated in FIG. 3, thermocouples or thermistors 206, 207 and 210 are provided located along electrode 47, which may be 2–20 centimeters in length. Each thermocouple or thermistor is provided with a pair of insulated wires (208, 209, 212), coupling them to the electrical connector located at the proximal end of the catheter. The thermocouples or thermistors may be displaced longitudinally and/or circumferentially from one another within or adjacent the electrode 47.

This catheter, as illustrated, is not provided with a deflection or steering mechanism, although it should be understood that a deflection mechanism as in the catheter of FIGS. 1 and 3 could readily be added. A tapered core wire 214 is provided, which assists in transmission of torque along the length of the catheter body. In use, the illustrated distal portion of the ablation catheter is delivered to the designed site within the heart by means of the deflectable guide catheter as shown in FIG. 2. Electrode 47 may be employed for cardiac ablation, with the functioning of thermocouples 206, 207 and 210 corresponding to that discussed above in conjunction with FIG. 3. Also illustrated are two areas 216 and 220 which are backfilled with adhesive, in order to provide a stable interconnection of the various catheter components.

The illustration is not intended to be to scale. As actually implemented, the illustrated design will allow for a substantially smaller catheter body, having a diameter on the order of three french. Tip electrode 52 may have a length on the order of 0.5–2 mm. Alternatively, tip electrode 52 may be replaced by a molded plastic tip, and conductor 202 deleted. In general, it is anticipated that tip electrode 52, if included, will be employed primarily for sensing of cardiac depolarizations and/or delivery of cardiac stimulation pulses, rather than ablation, due to its small size.

FIG. 5a illustrates the distal portion of an alternative embodiment of a catheter provided with multiple coil electrodes. Catheter 400 is provided with four adjacent coils 402, 404, 406 and 408, each of which may be approximately 5–10 mm length. Rather than being separated by circumferential insulators, the beginning of each coil is located closely adjacent the termination of the previous coil, and continues along the same helical path defined by the previous coil, so that the composite structure resembles a single coil having three breaks at 410, 412, 414. The adjacent ends of the electrode coils are preferably paced as closely adjacent as possible, and in any case spaced circumferentially from one another by less than one turn of the defined helix. A plastic tip member 418 or alternatively a tip electrode 418 is located at the distal end of the catheter. The coils are mounted partially embedded in a tubular plastic catheter body, with each electrode coil emerging through the catheter body 416 adjacent the termination of the previous coil, with the result that the mechanical characteristics of the catheter remain essentially constant along the length of the electrode coils. Further, if adjacent coils are simultaneously active, the electrode may generate an electrical field which creates thermal effects essentially indistinguishable from a single, continuous coil.

FIG. 5b is a cross sectional view through the catheter of FIG. 5a. In this view, the termination of coil 402, adjacent the point at which coil 404 begins is illustrated. The coils are shown partially embedded in catheter body 416, and insulated conductors 420, 422 and 424, in turn coupled to electrodes 404, 406 and 408 are visible in cross section. Paired wires 428, 430 and 432, in turn each coupled to a thermocouple (not illustrated) located internal to one of electrodes 404, 406, 408 are also visible, as is a tension or core wire 424. As illustrated, the catheter is provided with four electrode coils and four corresponding thermocouples, one for each electrode. However, greater or lesser numbers of electrodes and thermocouples may of course be employed.

FIG. 6a is a plan view of an alternative embodiment of a catheter according to the present invention. A handle 400 is provided at the proximal end of the catheter, and is in turn provided with an electrical connector 402. Mounted to the handle are two sliding knobs 404 and 408, employed to longitudinally move separate tension wires within catheter body 410. The structure and operation of knobs 404 and 408 and their associated tension wires are the same as the corresponding knob and tension wire described in detail in U.S. Pat. No. 5,487,757, cited above. Knob 406 is employed to rotate an internal, torqueing core wire, which extends within catheter body 410 to a point proximal to the electrodes 412, 416, 418, 420, 422 and 424. The structure and operation of knob 406 and its associated internal core wire also are the same as the corresponding knob and torquing core wire described in U.S. Pat. No. 5,487,757, cited above. The tension wire coupled to knob 408 extends to the distal tip of the catheter, while the tension wire coupled to knob 404 extends only to a point just proximal to the illustrated electrodes. The combination of the two tension wires and the core wire allow for the catheter to be deflected into a multiplicity of configurations, illustrated below. A tip electrode 426 is located at the distal end of the catheter.

FIG. 6b illustrates a side, plan view of the distal tip of the catheter illustrated in FIG. 6a. In this view, it can be seen that the electrodes 422 and 424, and correspondingly electrodes 412, 416, 418 and 420, illustrated in FIG. 6a, take the form of coil electrodes, similar to those illustrated in conjunction with the previous embodiments described above. However, in some embodiments of the invention, plural ring electrodes or other segmented electrode structures might be substituted. Exemplary dimensions for the inter-electrode spacing "A", the coil electrode length "B" and the tip electrode length "C" are 2 millimeters, 5 millimeters and 2 millimeters, respectively. Other dimensions and spacings, as well as other numbers of electrodes may correspondingly be substituted.

FIGS. 7a through 7d illustrate the deflection of the catheter illustrated in FIG. 6a due to longitudinal movement of the tension wires within the catheter body, coupled to knobs 404 and 408 (FIG. 6a). For purposes of understanding the illustrations, the deflectable portion of the catheter may be divided into two sections, including a distal section, 460 and an intermediate section, 450. The internal tension wire coupled to knob 408 (FIG. 6a) extends to the distal tip of distal section 460. The internal tension wire coupled to knob 404 (FIG. 6a) extends only to the distal end of intermediate section 450. The tension wires may be independently manipulated, so that each of sections 450 and 460 may be individually deflected, to produce separately adjustable curves.

Figure 7A:
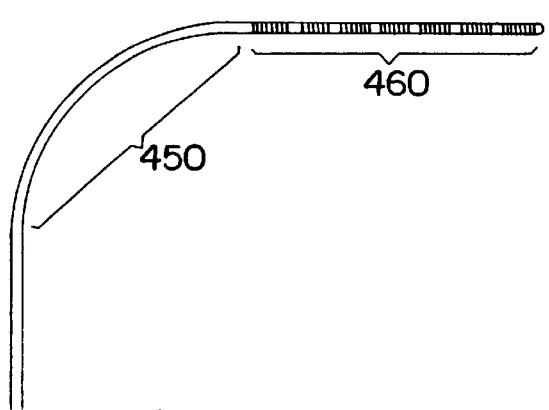
Figure 7C:
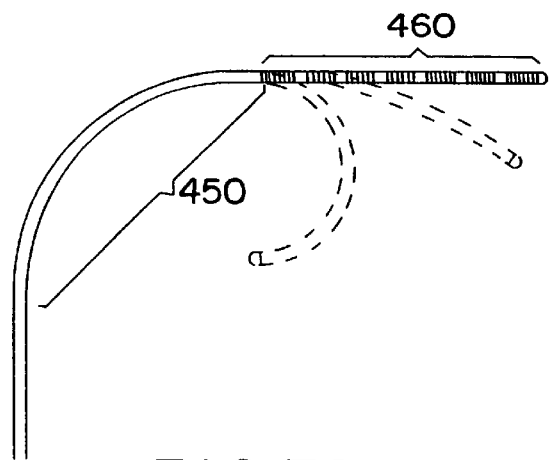
Figure 7B:
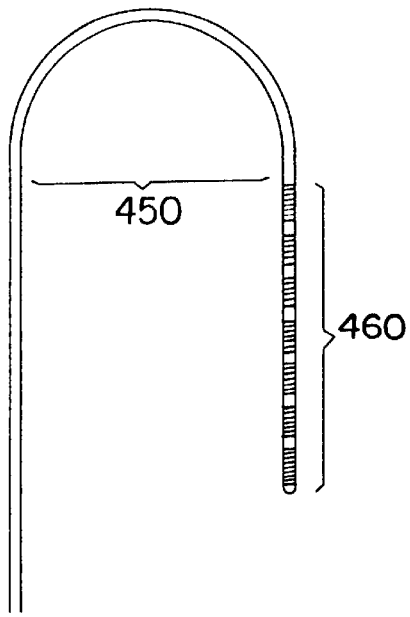
Figure 7D:
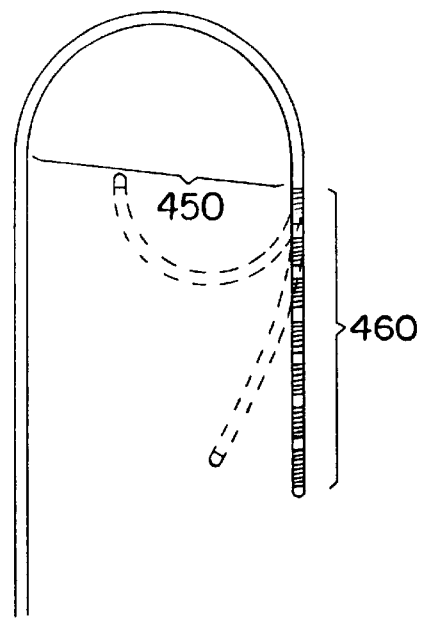

FIGS. 7a and 7b illustrate the deflection of intermediate section 450 in response to movement of 404 (FIG. 6). It should be noted that deflection of section 450 does not result in corresponding deflection of distal section 460. FIGS. 7c and 7d illustrate the deflection of distal section 460, due to movement of knob 408. It should be noted that as distal tip 460 deflects or is straightened, there is no significant additional deflection of intermediate section 450, and when both section 450 and 460 are deflected, the resulting curves lie generally in the same plane, in the absence of torque applied via the core wire associated with Knob 406 (FIG. 6a). The details of the deflection mechanism within the catheter are described in more detail below.

Figure 8:
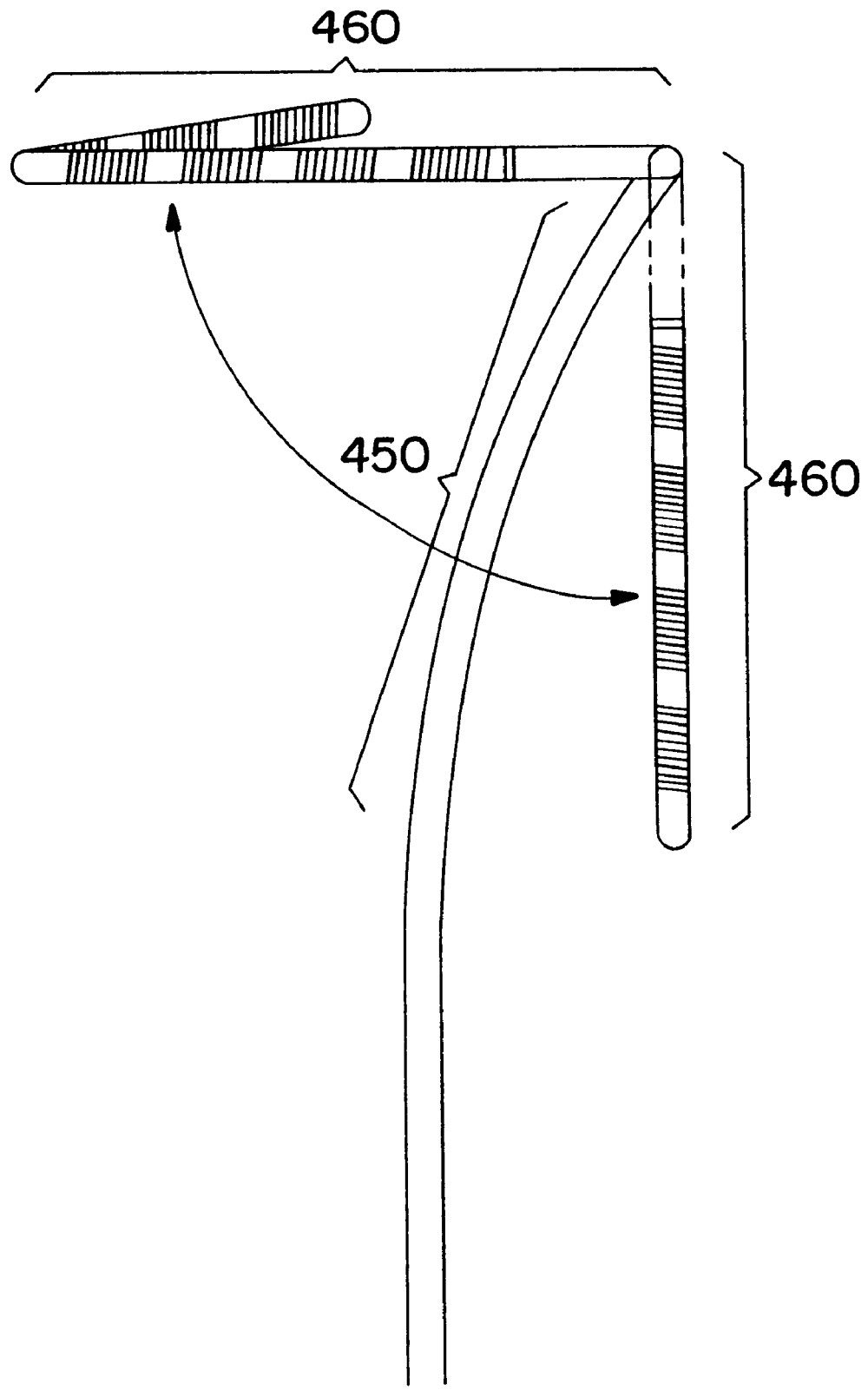

FIG. 8 illustrates the out of plane deflection of the catheter illustrated in FIG. 6a, due to rotation of knob 406. As illustrated, it is assumed that tension has been applied to both the tension wire coupled to knob 404 and tension wire coupled to knob 408 (FIG. 6), so that both the distal section 460 and the intermediate section of the catheter are deflected. As illustrated, rotation of the core wire causes twisting of the intermediate section 450 of the catheter, without corresponding deformation or deflection of the distal section of the catheter. The configuration of the distal section is thus unchanged by application of torque via knob 406 (FIG. 6a), but its orientation with respect to the axis of the catheter may be adjusted, causing the catheter to assume a variety of three-dimensional configurations. Alternatively, if only the distal section 460 is deflected by means of the tension wire coupled to knob 408 when torque is applied by knob 406, the intermediate section 450 is twisted without deflection so that the plane in which the deflected distal tip falls section 460 will simply be rotated around the axis of the catheter body.

Independent deflection of the distal and intermediate sections of the catheter is facilitated by employing extruded plastic tubes of differing flexibilities to form the catheter body. The flexibility of the distal portion of the catheter body may be 1.5 to 5 times the flexibility of the intermediate segment, with the intermediate segment in turn having a flexibility of 1.5 to 5 times that of the main catheter shaft. Preferably, the tube forming the distal section is at least three times as flexible as the tube forming the intermediate section and the tube forming the intermediate section is at least three times as flexible as the main catheter shaft.

FIG. 9a is a sectional view through the distal section of the catheter illustrated in FIG. 6a, in the vicinity of electrodes 422 and 424. Electrodes 422 and 424 are partially embedded in a silicone rubber sleeve 500, which surrounds an extruded Pebax tube 524, having a central lumen and a peripheral lumen. Lining the central lumen of tube 524 is a polyimide liner tube 526. Located within the peripheral lumen of tube 524 is tension wire 506, which is coupled to knob 408 (FIG. 6a). Located at the distal tip of tension wire 506 is a ball, 508 which engages a molded plastic insulator 502, to which tip electrode 426 is mounted. Space 504 between electrode 526 and insulator 502 is filled with an adhesive material. Electrode 426 is coupled to electrical connector 402 (FIG. 6) by means of an insulated conductor 510. Electrodes 422 and 424 are correspondingly coupled to the electrical connector by means of insulated conductors 512 and 516. Two thermocouples or thermistors 520 and 522 are provided adjacent electrodes 424 and 422, respectively, each coupled to electrical connector 402 (FIG. 6) by means of an insulated pair of wires, 514, 518. Proximal movement of tension wire 506 causes deflection of the distal section of the catheter as illustrated in FIGS. 7c and 7d.

FIG. 9b is a cross-sectional view through the portion of the catheter illustrated in FIG. 9a. In this view, the interrelation of silicone sleeve 500, extruded tube 524, liner tube 526, tension wire 506, and conductors 510, 512 and 514 can be appreciated.

FIG. 10a is a sectional view through the catheter of FIG. 6a in the vicinity of electrode 412, in the transitional region between the distal section of the catheter and the intermediate section of the catheter, and rotated 90 degrees from the sectional view of FIG. 9a. Visible in this view are extruded tube 524, silicone rubber sleeve 500 and polyimide liner tube 526, discussed above. For the sake of simplicity, insulated conductors connected to electrodes 414, 416, 418, 420, 422, 424 and 426, and to the thermocouple or thermistors associated therewith are illustrated schematically at 530. It should be understood that each of electrodes 412, 414, 416, 418, 420, 422 and 424 has an associated thermocouple or thermistor, with the structure of each electrode and associated thermocouple or thermistor being as illustrated in conjunction with electrodes 422 and 424 in FIG. 9a. Similar to the electrodes illustrated in FIG. 9a, electrode 412 is provided with an associated thermocouple or thermistor 550, and electrode 412 and thermocouple or thermistor 550 are coupled to the connector 402 (FIG. 6a) by means of conductors 552 and 528. The thermocouples or thermistors may be spaced only longitudinally from one another, all lying along one side of the distal portion of the catheter or they may also be circumferentially displaced from one another. It should be understood that additional thermocouples or thermistors might also be employed, so that each electrode is provided with more than one temperature sensor, in a fashion analogous to the multiple temperature sensors associated with electrode 47 illustrated in FIGS. 2 and 4.

A molded plastic insulator 554 defines the junction between the distal section of the catheter and the intermediate section. The catheter body in the intermediate section is fabricated of a multilumen extruded Pebax tube 560, which is provided with a central lumen and four peripheral lumens, spaced 90 degrees from one another. Tension wire 558 is illustrated located in one of the lumens extruded tube 560, and is provided with a ball shaped tip 564 which engages in a recess within insulator 554. Tension applied to tension wire 558 by means of knob 404, (FIG. 6*a*) causes deflection of the intermediate portion of the catheter. Passing through a second peripheral lumen of tube 560 is core wire 556 which is coupled to knob 406 (FIG. 6*a*), and is employed to twist the intermediate section of the catheter, as illustrated in FIG. 8, above. Polyimide tube 526 as illustrated extends past the proximal most portion of insulator 554, and is bonded to the interior of tube 560 by means of an adhesive at 562.

FIG. 10*b* illustrates a cross-section through the intermediate section of the catheter of FIG. 6*a*, showing the location of tension wire 558, tension wire 506 and core wire 556. In this view it can be seen that tension wire 506 is displaced 90 degrees from tension wire 558. Nonetheless, when both wires are tensioned, the resultant curves lie generally, although not precisely, in the same plane. As a practical matter, the less the two tension wires are displaced from one another, the closer the two curves formed in the distal and intermediate sections will come to falling in precisely the same plane in the absence of torque applied via core wire 556, and if closely coplanar curves are desired, the two tension wires should be located in closely adjacent lateral lumens or in the same lateral lumen.

FIG. 10*c* illustrates a cross-section through the catheter located along the proximal, inner surface 554*a* of the insulator 554. In this view, it can be seen that the insulator 554 is provided with four bores aligned corresponding to the four peripheral lumens of extruded tube 560. In this view, the ball tip 564 of tension wire 558 is visible, along with tension wire 506. In this view it can also be seen that the distal tip of core wire 556 extends through one of the bores through insulator 554, it is then looped back to reenter a second, adjacent bore, allowing for torque to be applied to insulator 554 by means of rotation of core wire 556. The various conductors coupled to the electrodes and thermocouples or thermistors are illustrated generally at 530.

FIG. 10*d* illustrates a cross sectional view through the distal tip portion of the catheter, slightly proximal to insulator 554. The illustrated elements correspond to those shown in FIG. 9*d*.

FIG. 11*a* is a side, sectional view through the transition portion of the catheter, where the intermediate section of the catheter is joined to the main catheter body. In this view, extruded tube 560, tension wire 558, tension wire 506, core wire 556 and insulated conductors 530 are all visible, corresponding to the elements illustrated in FIG 10*a*. Proximal to the intermediate portion of the catheter, the catheter is provided with a reinforced Pebax tube 570 provided with internal stainless steel braiding 574 and a polyimide inner liner tube 572. As illustrated, at the transition from the reinforced braided tube 570 to multi-lumen extruded tube 560, core wire 556 and tension wires 506 and 558 each enter a respective one of the four peripheral lumens of the extruded tube 560, preceding distally therein until they reach insulator 554 (FIG. 10*a*). Reinforced tube 570 extends proximally to the catheter handle 400 (FIG. 6*a*).

FIG. 11*b* illustrates a cross-section through the catheter body, located proximal to the intermediate section of the catheter. Elements illustrated in FIG. 11*b* correspond to those illustrated in FIG. 11*a*.

Figure 12A:
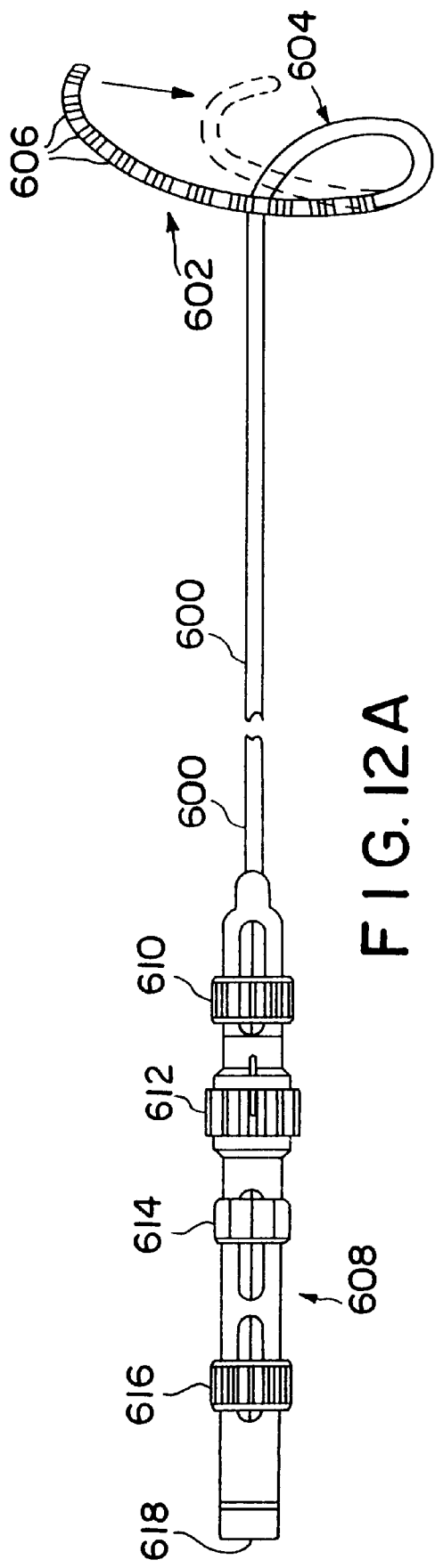
FIG. 12a illustrates a plan view of a mapping catheter according to the present invention.

FIG. 12*a* is a perspective view of a mapping catheter employing the deflection mechanism of the catheter illustrated in FIGS. 6–11. The catheter is provided with an elongated catheter shaft 600, with an intermediate section 604 and a distal section 602 which carries mapping electrodes 606. Distal section 602 and intermediate section 604 are each provided with a corresponding internal tension wire operative precisely as in the catheter illustrated in FIGS. 6–11, coupled to knobs 614 and 610 on handle 608. An internal torquing core wire is also provided coupled to the distal end of the intermediate section 604 and operative as described above to cause the plane defined by the curve of the distal section to be varied relative to the plane of the curve of the intermediate section 602. Electrodes 606 are all individually coupled to electrical connector 618 by means of insulated wires within catheter body 600.

Figure 12B:
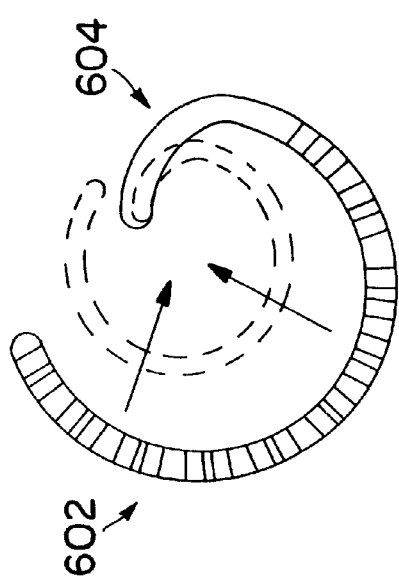

As an optional additional feature, the catheter is provided with an internal sliding core wire as discussed above, which when displaced longitudinally by means of knob 616 on handle 608 varies the arc of curvature of the distal and/or intermediate sections of the catheter, according to the teaching of pending allowed U.S. Pat. No. 5,487,757, incorporated by reference above. Knob 616 and its associated core wire may be the same as the corresponding elements in the '757 patent. FIG. 12*b* illustrates variation in the arc of curvature of distal section 602 due to movement of the sliding core wire discussed above.

Figure 13:
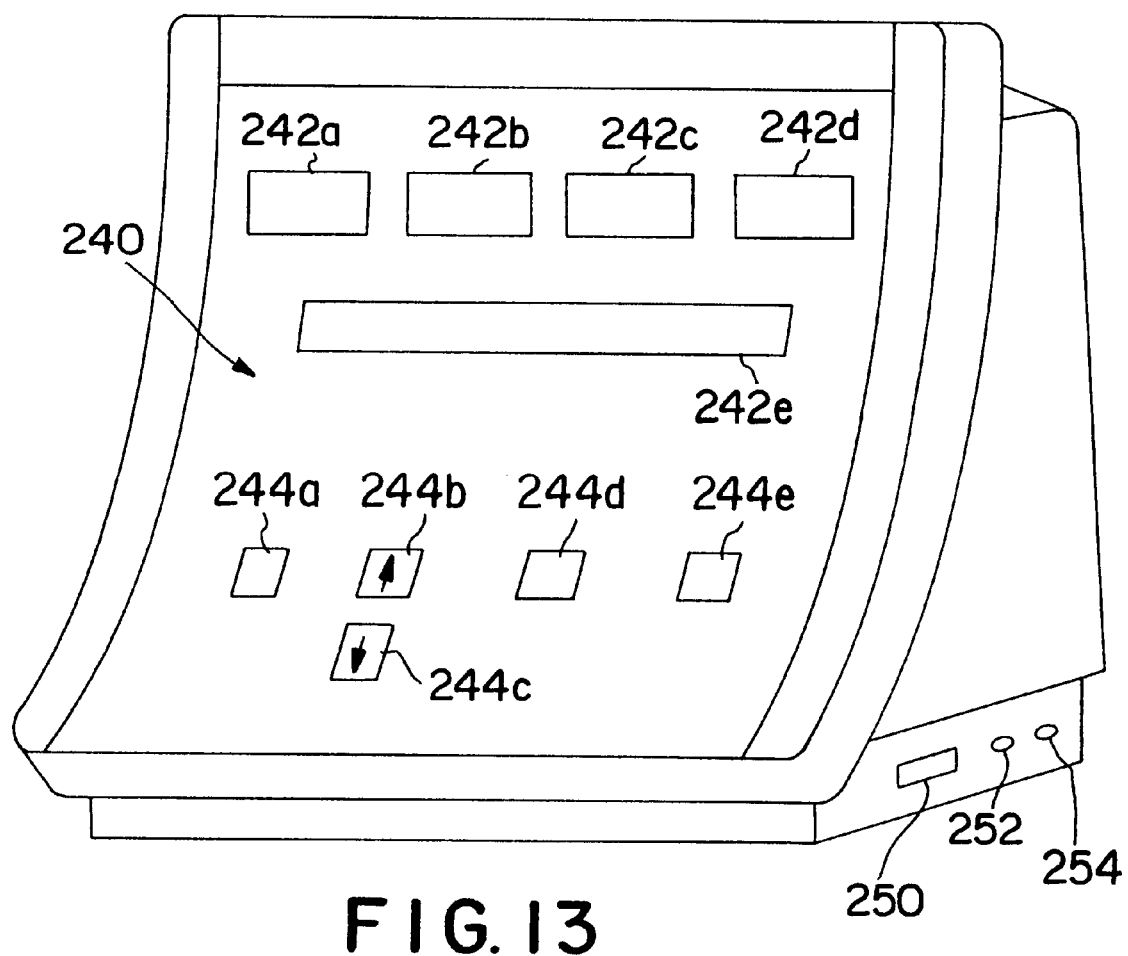
FIG. 13 is a perspective view of an RF power source for use with the catheters of FIGS. 1–11.

FIG. 13 is a perspective view of an R-F power source for use with the catheters described above. This R-F power source for the catheters is based upon Similar R-F power sources U.S. Pat. No. 5,573,533 issued Nov. 12, 1996 and U.S. Pat. No. 5,540,681 issued Jul. 30, 1996 both of which are incorporated by reference in their entireties. The radio-frequency generator includes a user interface panel 240 having a plurality of displays and indicators 242, and switches 244 to permit the operator to monitor and control delivery of power to the catheter. The panel 240 includes a first display 242*a* which provides a continuous digital readout of the actual radio-frequency power being delivered. A second display 242*b* shows the actual electrode temperature or temperatures measured by the temperature sensors within the catheter. A third display 242*c* shows the calculated impedance or impedances (based on measured current and voltage) between the catheter ablation electrode or electrodes and an indifferent electrode during the delivery of radio-frequency energy. The indifferent electrode is attached to the patient and provides a return path to complete the circuit to the ablation electrode or electrodes, and may take the form of a plate electrode or may be one of the various electrodes located on the catheter in use. A sudden rise in impedance indicates that coagulum has formed on the corresponding ablation electrode, which should be removed. A fourth display 242*d* provides an indication of the time that radio-frequency power has been delivered during an ablation procedure.

The panel 240 further includes an alphanumeric display 242*e* which presents additional information to the user, depending on the operational mode selected as described below. Such information may include the set point for either temperature (in ° C.) or power (in Watts), depending on the control mode, the total number of times that power supply to the ablation electrode has been initiated, and the total elapsed time that the radio-frequency power has been delivered from the time power to the generator was turned on. Finally, the display 242e may indicate the available ranges for power, temperature, or time, depending on the variable which is being set within the system. Display 242e may further provide user warnings, including excessively high temperature, unacceptable catheter, excessively high impedance, low impedance, and excessively high power, as described in the above cited applications. Finally, a visual or audible indicator may be provided to indicate when the battery charge has become low, typically when it reaches 25% of capacity.

Switch 244a is provided in order to select the control mode, e.g., either power or temperature. A particular set-point (temperature or power) will be adjusted by raising or lowering the set point using the appropriate up or down switch 244b or 244c. The time set-point is adjusted by pressing RF timer switch 244d and simultaneously raising or lowering the set point using up or down switch 244b or 244c. Switch 244e initiates the delivery of R-F power, causing R-F power to be delivered until either the switch 244e is again pressed or the time set-point is reached. If a warning condition occurs (i.e., high power or high impedance), delivery of R-F power is terminated. A main off and on switch 248, a catheter connector 250, an indifferent electrode connector 252, and a foot pedal connector 254 are also provided.

Additional connections to the radio-frequency generator will usually include an ECG connector, an analog output connector which permits output to a multi-channel chart recorder for recording radio-frequency power, impedance between the ablation electrode and indifferent electrode, and ablation electrode temperature. An additional connector will usually be provided to permit connection of the internal microprocessor to an external computer to monitor and temporarily override programming in the PROMS. A switch may also be provided to permit the operator to set the volume level of the tone during the R-F ablation. Finally, an equipotential connector will be provided for connection to an external ground.

As illustrated in the figures above, the catheters according to the present invention are provided with one or more ablation electrodes, each of which may be individually activated by means of a separate insulated conductor and two or more temperature sensors, each of which may be individually monitored, in order to determine the temperature of each of the ablation electrodes. As will be discussed in more detail below, the temperature sensors may be employed to control delivery of R-F energy to the electrodes in a variety of ways. In a first, simpler embodiment, R-F energy is applied from a common source to all ablation electrodes. In this case, the R-F source may be regulated either by measuring the temperature at each temperature sensor individually, and employing the highest of the measured temperatures to control R-F power applied to the electrodes, or alternatively, the outputs of the temperature sensors may be averaged, and the average value used to control the R-F power applied to the electrodes. An appropriate control algorithm for controlling R-F power as a function of measured temperature is set forth in the allowed applications cited above. Alternatively, any of the numerous temperature based control systems employed in conjunction with presently available radio frequency ablation catheters may also be employed in conjunction with the present invention.

In a somewhat more complex embodiment of the present invention, each individual electrode employed for ablation purposes may be provided with an independently controllable power source, with power applied to each individual electrode regulated by means of one or more temperature sensors associated with each electrode. In this embodiment, in the event of hot spots developing adjacent an individual electrode, power applied to this electrode may be reduced or shut off entirely in order to avoid burning. In this embodiment, the on times of the R-F signal applied to each individual electrode may vary. Electrodes which are in closer or better contact with the tissue may as a result have a shorter on time, while electrodes with a poorer contact with body tissue have a longer on time, allowing for a greater likelihood that an effective lesion will be produced which, extending along entire length of the elongated electrode surface defined by the electrodes involved.

Figure 14:
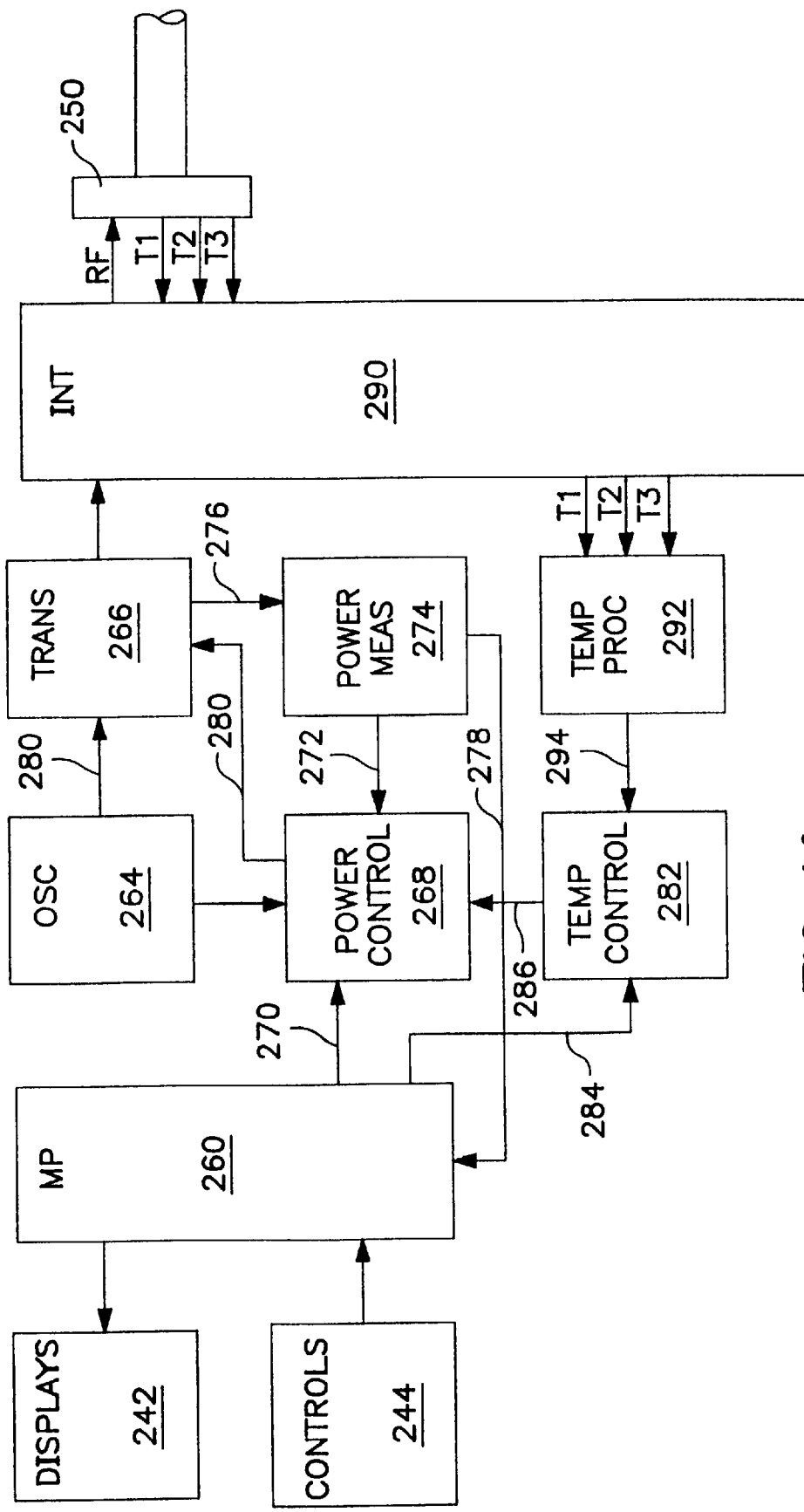
FIG. 14 is a functional block diagram of an RF power source for use in conjunction with the catheters of FIGS. 1–11.

FIG. 14 is a functional block diagram of a first embodiment of an R-F power supply as illustrated in FIG. 13. Front panel displays 242 and controls 244 are connected to a digital microprocessor 260, such as an INTEL 80C 186, which permits interface between the user and the remainder of the electrical components of the system. In particular, the microprocessor 260 provides for monitoring of power, current, voltage, temperature and battery level. As necessary, the microprocessor will provide this information to the appropriate display and/or indicator 242 on the front panel 240. Additionally, the microprocessor 260 permits the user to select the control mode (either temperature or power) and to input the power set point, temperature set point, and timer set point to the system.

The primary source of power for the radio-frequency generator may be a 12 V battery rated at 7.2 ampere-hours. A back-up battery (not shown) such as a lithium cell may also be provided to provide sufficient power to the microprocessor 260 to maintain desired memory functions when the main power from the 12 V battery is shut off.

A crystal-locked radio-frequency oscillator 264 generates the switching pulses which drive both the power transformer 266 and the power controller 268. Power controller 268 is an analog controller which operates by pulse-width modulation by comparing a power set point signal on line 270 from microprocessor 260 with an actual power signal generated by a power measurement circuit 274, typically including a torroidal transformer coupled to the power output 276 from the transformer 266. The power measurement component 274 multiplies the output current and voltage and provides the resulting actual power signal to both the power controller through line 272 and the microprocessor through line 278. The R-F power output of transformer 266 is provided to interface board 290, and thereby is provided to the ablation electrode or electrodes on the catheter. Separate analog comparator circuits (not illustrated) may also be provided for monitoring the output of the power measurement component 274 in order to shut-off current to the output transformer 266 if the power exceeds a limit, typically 55 watts. Power transformer 266 includes a center tap which receives the output 280 of the analog power controller 268. A secondary winding of the transformer provides for continuous monitoring of the applied voltage in order to permit the power calculations by power measurement circuit 274.

Analog temperature controller 282 is provided to permit operation in a temperature control mode. A temperature set point is delivered to the temperature controller 282 from the microprocessor 260 through line 284. Temperature controller 282 operates on a proportional control mode, producing a power set point signal on line 286, based upon the difference between the temperature set point on line 284 and the signal on line 294 indicative of a temperature measured by the thermocouples within the catheter. The resultant power set point is fed to the power controller 268. The power set point signal on line 286 replaces the set point signal on line 270 when the system is in temperature control mode operation. The analog power controller 268 thus acts as a cascade control loop in a two-stage temperature control protocol. It has been found that such two-stage analog control permits precise and very fast control of power to maintain the desired temperature set point at the ablation electrode. Separate analog comparator circuits, not illustrated, may also be provided for monitoring the temperature or temperatures of each of the temperature sensors in order to shut-off current to the output transformer if the temperature measured at any temperature sensor exceeds a limit, typically about 100° C. Appropriate comparator circuits are illustrated in U.S. Pat. Nos. 5,573,533 and 5,540, 681 cited above.

Temperature processing circuit 292 processes the signals from the temperature sensors within the catheter to provide a combined signal on line 294 which is provided temperature control 294. The combined signal may be indicative of the average value of the signals from the temperature sensors, or may correspond to the signal from the temperature sensor indicating the highest temperature.

All external connections to the radio-frequency generator will be made through an interface board 290. The interface board 290 permits connection of the main battery and back-up battery (not illustrated), as well as the catheter connector 250, the ECG connector, the data recorder connector, and the like. Connection of the temperature sensors is preferably optically isolated from the internal components of the radio-frequency generator. The data recorder outputs on the R-F generator may also be optically isolated if necessary to reduce signal noise.

In the embodiment illustrated in FIG. 13, above, the R-F signal is a square wave signal. However, some operating environments require that the square wave generated by the crystal-locked radio-frequency oscillator 64 be filtered to round off the square edges to provide a sinusoidal instead of pulsed R-F signal. At high-power this filtering causes undesirable signal attenuation. An alternative power modulating system that obviates the need for filtering and is particularly useful for high-power applications is depicted in the above-cited U.S. Pat. No. 5,540,681.

Figure 15:
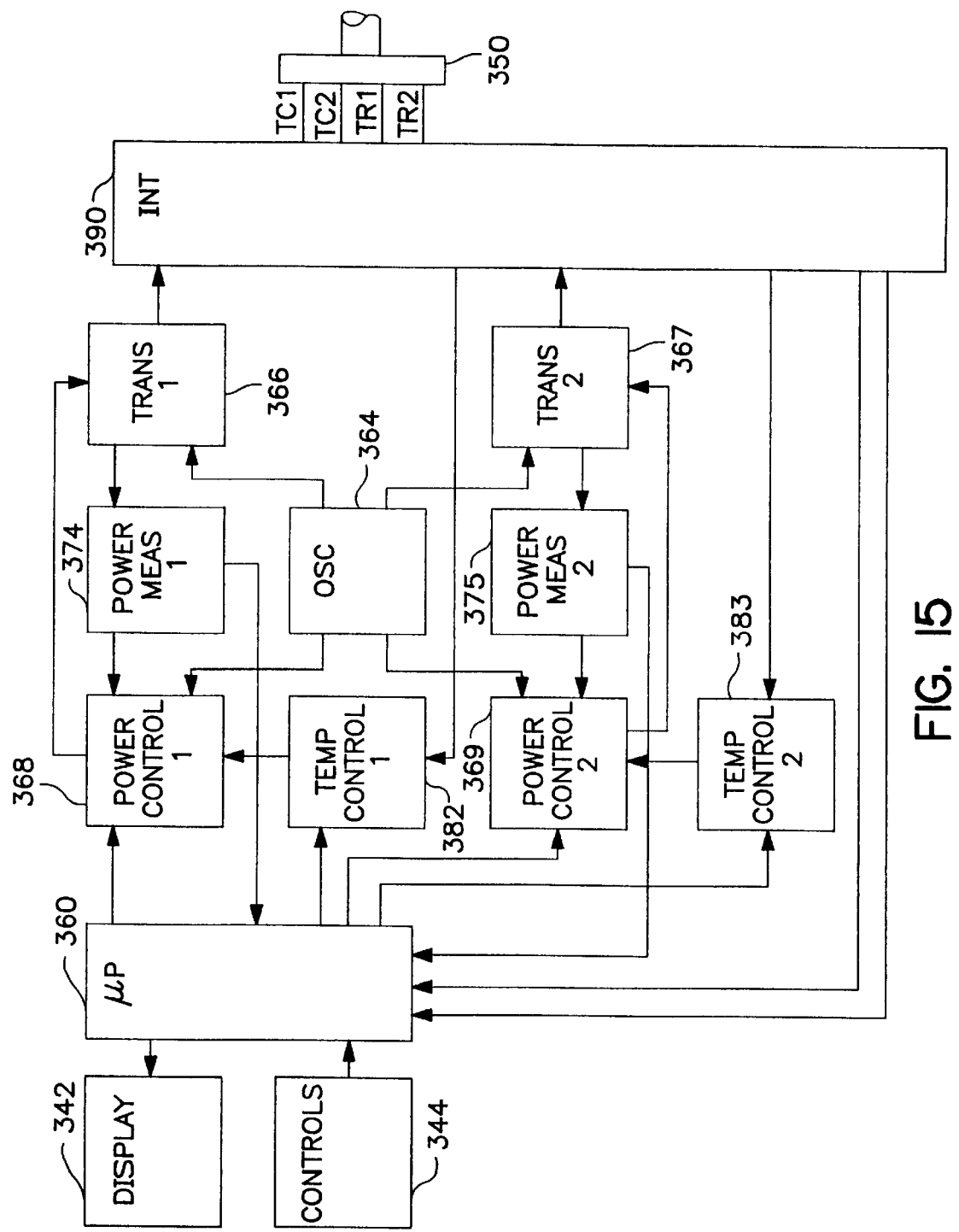
FIG. 15 is a functional block diagram of a second embodiment of a power source for use in conjunction with the catheters illustrated in FIGS. 1–11.

FIG. 15 illustrates an alternate embodiment of an R-F power supply system for use in conjunction with the present invention. In this embodiment, separately controllable R-F outputs are provided for individual ablation electrodes on the catheter, as discussed above. In this Figure, the functions of display 342 and controls 344 correspond to display 242 and controls 244, illustrated in FIG. 13, with the exception that displays are provided for the temperature, impedance, and so forth for each ablation electrode and associated R-F power supply. Microprocessor 360 similarly corresponds to microprocessor 260, with the exception that it provides individual control outputs to and receives individual input signals from the components of each of the two included R-F power supplies.

The first R-F power supply includes oscillator 364, transformer 366, power control 368, power measurement circuit 374 and temperature control circuit 382, which correspond precisely to oscillator 264, transformer 266, power control 268, power measurement circuit 274 and temperature control circuit 282, illustrated in FIG. 6. The second R-F power supply includes oscillator 364, shared with the first R-F power supply, transformer 367, power control 369, power measurement circuit 375 and temperature control circuit 383, which also correspond precisely to oscillator 264, transformer 266, power control 268, power measurement circuit 274 and temperature control circuit 282, illustrated in FIG. 8. Each of the two power supplies receives a signal from one of the thermocouples in the catheter, and regulates power applied to the electrode adjacent the that thermocouple. Correspondingly, each of the two power supplies may be provided with analog comparators for sensing power and temperature as discussed above.

In this embodiment, each of the ablation electrodes is individually regulated, so that the electrodes may be supplied with differing levels of power, and may be activated for different periods of time. The flexibility of this approach allows the system to take differences in tissue condition, electrode contact and other variables into account and increases the likelihood that a lesion will be produced extending for the entire length of the electrodes selected.

As a further refinement to either of the embodiments illustrated in FIGS. 13 and 14, the controls 244, 344 may be expanded to include switches which selectively disable or enable individual electrodes, and/or temperature sensors allowing the physician to control the effective length of the electrode surface available for ablation and to adapt the temperature control mechanism to the needs of an individual patient. Alternatively, catheters may be provided with varying numbers of temperature sensors, electrodes or electrode dimensions, in order to allow the physician to accomplish a similar result by catheter selection.

Figure 16:
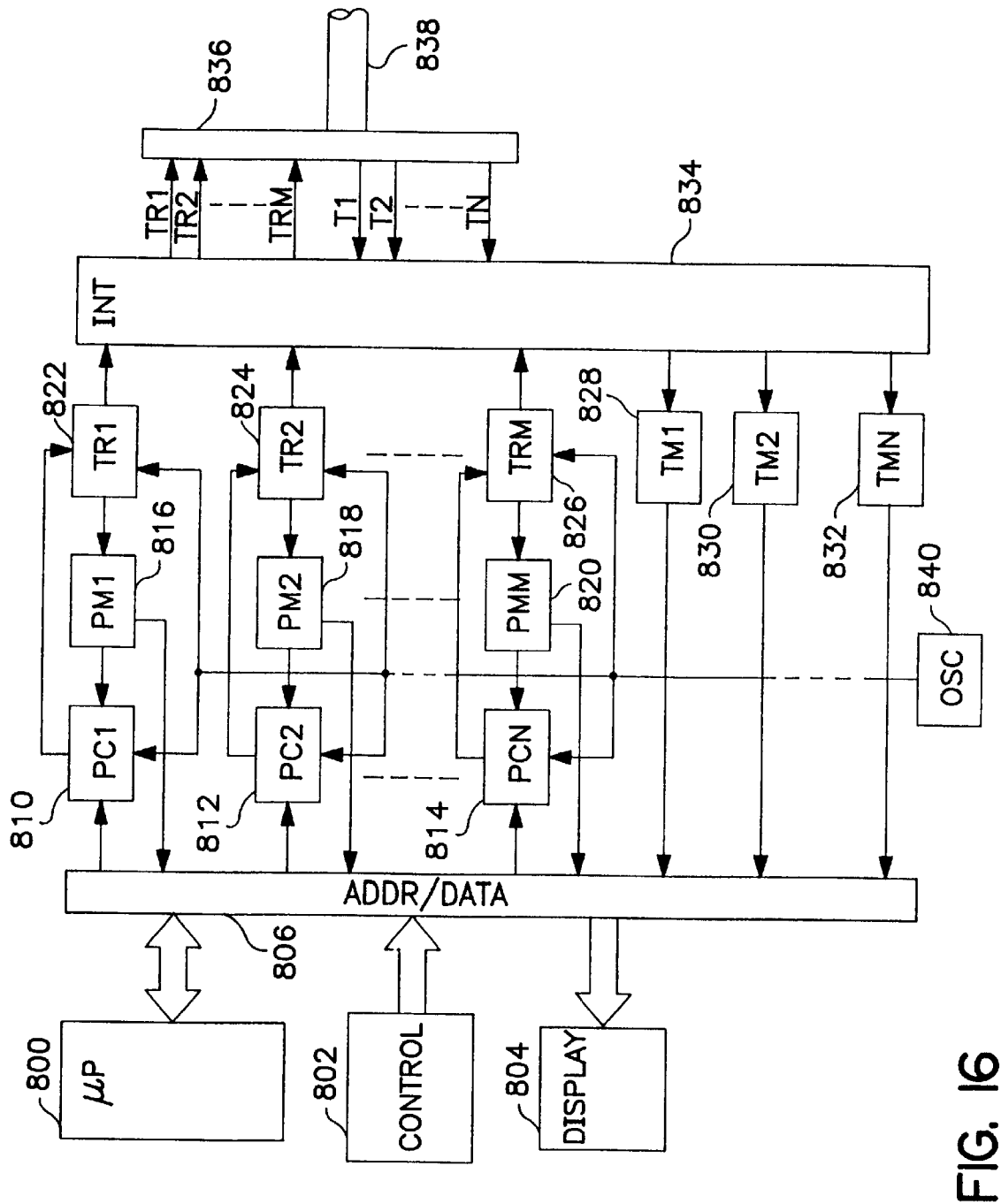
FIG. 16 is a functional block diagram of a third embodiment of a power source for use in conjunction with the catheters illustrated in FIGS. 1–11.

FIG. 16 illustrates yet another alternate embodiment of an R-F power supply system for use in conjunction with the present invention. In this embodiment, separately controllable R-F outputs are provided for individual ablation electrodes on the catheter, as discussed above. In this Figure, the functions of display 804 and controls 802 correspond to display 342 and controls 344, illustrated in FIG. 14. Microprocessor 800 similarly corresponds to microprocessor 360, with the exception that it is illustrated as providing control outputs to and receiving input signals from the remaining circuitry on address/data bus 806. The power supply system as illustrated includes a desired number "M" of individually controllable R-F power supplies and receives temperature inputs from a desired number "N" of temperature sensing devices in the catheter, illustrated schematically at 838.

Each R-F power supply includes a transformer (822, 824, 826), a power control circuit (810, 812, 814), a power measurement circuit (816, 818, 820) which correspond precisely to oscillator 364, transformer 366, power control 368 and power measurement circuit 374, illustrated in FIG. 14. All R-F power supplies share oscillator 840, corresponding to oscillator 364 in FIG. 14. Instead of analog temperature control circuits (368, 383, FIG. 14) the illustrated power supply system employs software controlled temperature processing, accomplished by microprocessor 800, which receives the "N" temperature input signals from temperature measurement circuits (828, 830, 832, each of which are coupled to a corresponding temperature sensor in catheter 838 by means of the electrical connector on the catheter, illustrated schematically at 836 and interface circuit 834, which corresponds to interface 390 illustrated in FIG. 14.

Processor 800 receives the "N" temperature signals and, based upon the indicated temperatures, defines power set points for each of the power control circuits (810, 812, 814), which in the manner described above control the power levels applied to electrodes on the catheter through interface 834. Processor 800 may also selectively enable or disable any of the "M" provided R-F power supplies, in response to external control signals from controls 802 or in response to detected anomalous temperature conditions, as discussed below.

Processor 800 may define power set-points for one or more electrodes as described above, based upon average temperature values from a plurality of temperature sensors, based on the highest indicated temperature from a plurality of temperature sensors, or in the case of a catheter having one temperature sensor associated with each of a plurality of electrodes may determine the power set-point for each electrode from a single temperature sensor. The processor 800 may also process the indicated temperatures from the temperature sensing circuits (828, 830, 832) to allow for selective disablement of individual temperature sensors and/or individual R-F power supplies. Particularly in catheters which have one or more electrodes, each of which is provided with multiple temperature sensing devices, the processor may read the indicated temperatures associated with the individual temperature sensing devices, compare the temperatures and, if the sensed temperature differential exceeds a preset value reduces the power set-point of the electrode, disables power delivery to the electrode entirely, or causes an alarm to sound.

The processor may identify individual failed temperature sensors using a number of techniques. First, the processor 800 may compare each temperature sensor'is indicated temperature with body temperature, prior to activation of the R-F power supply circuits. In the event the indicated temperature for a sensor differs by more than a pre-set value from normal body temperature, the corresponding temperature sensor'is indicated temperature would not be employed for control purposes. Second, the processor may monitor the rate of change of the indicated temperatures of each temperature sensor to determine whether the rate of change exceeds a pre-set value, and, if so disables the failed temperature sensor. Third, if the catheter is provided with multiple temperature sensors which are located closely adjacent to one another, the processor 800 may compare the indicated temperatures for each temperature sensor, and if one indicated temperature differs from that indicated other closely adjacent temperature sensors by more than a pre-set value, may disable the disagreeing sensor. Fourth, the processor may compare each temperature sensor'is indicated temperature with a set range of indicated temperatures associated with normal operation of the sensors and disable any temperature sensing device found to be out of range. More than one or all of these four techniques may be employed simultaneously. If multiple temperature sensors are provided for each electrode., the processor 800 may simply employ the remaining temperature sensors to monitor the electrode associated with a failed sensing device. If an electrode is found to have no operative temperature sensors, the processor 800 may employ a temperatures or temperatures indicated by a temperature sensor or sensors associated with an adjacent electrode or electrodes to monitor the electrode associated with the failed sensor.

The catheters may have differing configurations than those illustrated. For example, while the ablation catheter illustrated in FIG. 2 introduced by means of a guiding catheter displays a generally straight configuration, a pre-curved configuration could be provided at its distal end, such as a spiral configuration, and/or the deflectable guide catheter might be replaced by a pre-curved guiding catheter or sheath. While the elongated ablation electrodes illustrated are metal coil electrodes, electrodes of other conductive materials and taking other forms, such as tubular braids or series of ring electrodes may also usefully be employed in the context of the present invention. Similarly, while the disclosed embodiment employs an R-F power source or sources, other power sources, e.g. microwave sources, D-C sources may be employed in the context of the inventive temperature controlled system. Finally, while the temperature sensing devices associated with each electrode as illustrated are located internal to the catheters, they may alternatively be exposed to the exterior of the catheter adjacent the electrode to be monitored. As such, the embodiments disclosed in the above specification should be considered exemplary, rather than limiting, with regard to the following claims.

We claim:

1. A catheter ablation system, comprising:
    an elongated catheter body having a distal segment;
    at least one electrode, extending along said distal segment;
    a plurality of temperature sensors, arranged along said distal segment, adjacent said at least one electrode and providing outputs indicative of temperature;
    a power source means for providing a power output to said at least one electrode; and
    temperature processing means, coupled to said outputs of said temperature sensors and to said power source, for controlling power output from said power source to said at least one electrode as a function of said outputs of said plurality of temperature sensors, wherein said temperature processing means comprises means for comparing temperatures indicated by outputs of said temperature sensors to a known temperature and means for disabling subsequent use of the output of a said sensor to control said power output, if the output of said sensor differs from said known temperature by more than a defined value.

2. A system according to claim 1 wherein said defined temperature is normal body temperature.

3. A catheter ablation system, comprising:
    an elongated catheter body having a distal segment;
    at least one electrode, extending along said distal segment;
    a plurality of temperature sensors, arranged along said distal segment, adjacent said at least one electrode and providing outputs indicative of temperature;
    a power source means for providing a power output to said at least one electrode; and
    temperature processing means, coupled to said outputs of said temperature sensors and to said power source, for controlling power output from said power source to said at least one electrode as a function of said outputs of said plurality of temperature sensors, wherein said temperature processing means comprises means for monitoring rates of change of temperatures indicated by outputs of said temperature sensors to a defined rate of change and means for disabling subsequent use of the output of a said sensor to control said power output, if the rate of change of the output of said sensor differs from said defined rate of change by more than a defined value.

4. An ablation power supply, comprising:
    input means for receiving outputs of a plurality of temperature sensors indicative of temperature;
    a power source means for providing a power output to at least one ablation electrode;

temperature processing means, coupled to said input means and to said power source, for controlling power output from said power source to said at least one electrode as a function of said outputs of said plurality of temperature sensors, wherein said temperature processing means comprises means for comparing temperatures indicated by outputs of said temperature sensors to a known temperature and means for disabling subsequent use of the output of a said sensor to control said power output, if the output of said sensor differs from said known temperature by more than a defined value.

5. A system according to claim 4 wherein said defined temperature is normal body temperature.

6. An ablation power supply, comprising:

input means for receiving outputs from a plurality of temperature sensors indicative of temperature;

a power source means for providing a power output to at least one ablation electrode; and temperature processing means, coupled to said input means and to said power source, for controlling power output from said power source to said at least one electrode as a function of said outputs of said plurality of temperature sensors, wherein said temperature processing means comprises means for monitoring rates of change of temperatures indicated by outputs of said temperature sensors to a defined rate of change and means for disabling subsequent use of the output of a said sensor to control said power output, if the rate of change of the output of said sensor differs from said defined rate of change by more than a defined value.

* * * * *